United States Patent [19]

Takee et al.

[11] Patent Number: 5,081,280
[45] Date of Patent: * Jan. 14, 1992

[54] PROCESS FOR THE PRODUCTION OF ESTER COMPOUNDS

[75] Inventors: Koichi Takee; Masayoshi Gohbayashi; Kunihide Oka, all of Nakatsu, Japan

[73] Assignee: Yoshitomi Pharmaceutical Industries, Ltd., Osaka, Japan

[*] Notice: The portion of the term of this patent subsequent to Dec. 5, 2006 has been disclaimed.

[21] Appl. No.: 319,687

[22] Filed: Mar. 7, 1989

[30] Foreign Application Priority Data

Mar. 18, 1988 [JP] Japan .................. 63-66834
May 30, 1988 [JP] Japan ................. 63-133682

[51] Int. Cl.$^5$ .............................................. C07C 69/76
[52] U.S. Cl. ...................................................... 560/75
[58] Field of Search ........................................ 560/75

[56] References Cited

U.S. PATENT DOCUMENTS

| | | | |
|---|---|---|---|
| 3,644,482 | 2/1972 | Dexter et al. | 260/473 R |
| 3,944,594 | 3/1976 | Kleiner et al. | 260/473 S |
| 4,228,297 | 10/1980 | Haeberli et al. | 560/75 |
| 4,417,071 | 11/1983 | Rosenberger | 560/75 |
| 4,536,593 | 8/1985 | Orban | 560/75 |
| 4,618,700 | 10/1986 | Gubler et al. | 560/67 |
| 4,739,102 | 4/1988 | Tokunaga | 560/75 |
| 4,754,045 | 6/1988 | Sasaki et al. | 549/335 |
| 4,885,382 | 12/1989 | Gohbayashi | 560/75 |

FOREIGN PATENT DOCUMENTS 0300055 1/1989 European Pat. Off. .

OTHER PUBLICATIONS

Iwamoto et al., Chem. Abstr., vol. 75 (1971), p. 476, No. 20535e.
Mitsui Petrochem. Ind. K.K., Abstract of JP 79 86447, 7.10.79.

*Primary Examiner*—Paul J. Killos
*Attorney, Agent, or Firm*—Wenderoth, Lind & Ponack

[57] ABSTRACT

In producing ester compound useful as an antioxidant for organic materials which are represented by the formula:

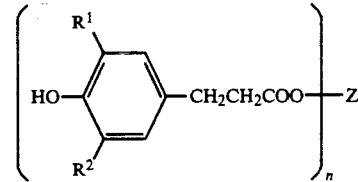

wherein $R^1$ and $R^2$ are the same or different and represent hydrogen or straight or branched chain alkyl radicals containing 1-8 carbon atoms, Z is an organic radical derived from an n-hydroxy alcohol, and n denotes an integer of 1 to 4, by transesterification, monoalkyltin compounds are used as a catalyst, whereby the ester compounds can be produced with high quality and in high yields.

3 Claims, No Drawings

PROCESS FOR THE PRODUCTION OF ESTER COMPOUNDS

BACKGROUND OF THE INVENTION

Sterically hindered phenolic compounds, for example, tetrakis[3-(3,5-di-tert-butyl-4-hydroxyphenyl)propionyloxymethyl] methane, octadecyl 3-(3,5-di-tert-butyl-4-hydroxy-phenyl)propionate, triethylene glycol bis[3-(3-tert-butyl-4-hydroxy-5-methylphenyl)propionate], 3,9-bis{2-[3-tert-butyl-4-hydroxy-5-methylphenyl)-propionyloxy]-1,1-dimethylethyl}-2,4,8,10-tetraoxaspiro[5·5] undecane or the like have been used as an antioxidant for organic materials such as polyolefines.

These compounds are generally produced by submitting corresponding alkyl propionates and alcohols to transesterification, for which basic catalysts such as alkali metal hydrides, alkali metal alkoxides, alkali metal amides, dibutyltin oxide, zinc salts, calcium salts or the like are used, as disclosed in U.S. Pat. Nos. 3,644,482, 3,944,594, 4,228,297, 4,618,700, 4,739,102, 4,754,045, etc. By the use of these catalysts, however, the production of the hindered phenols as mentioned above requires a long reaction time and causes the reaction solution to be colored in brown, and accordingly, does not afford products commercially presentable. With Dibutyltin oxide is superior to the other catalysts in respect of the reaction time, but still is susceptible to coloration and after the reaction, the resulting solution is yellow or yellowish-brown Interception from air, or any other measure for the prevention of coloration is thus a big consideration. The catalyst is difficult to remove or cannot be removed completely, particularly in a purification process such as recrystallization, and consequently, it is difficult to suppress its content within the allowable concentration of products. A method of obtaining the intended products by distillation is also known. However, the distillation process requires a long time and a high temperature upward of 240° C. with the result that the products are colored.

In the case of tetrakis[3-(3,5-tert-butyl-4-hydroxyphenyl)propionyloxymethyl]methane, U.S. Pat. No. 4,618,700 discloses a process for transesterification wherein 4.6–6.0 moles of the propionates per 1 mole of pentaerithritol are used and the excess propionates are recovered. This reaction per se was advantageous in that it was terminated in a short period of time, but required a long time for the distillation to recover a large amount of the unreacted excess propionates. Eventually, it took nearly the same period of time as the case with the reaction wherein about 4.4 moles of the propionates were used.

Considering the fact that recycling of the recovered propionates is limited to two times because of accumulation of decomposed propionates and the fact that the distillation for the separation of the products brings about the afore-mentioned disadvantages, this method is not industrially feasible.

Heretofore, in preparing this tetrakisester compound, an unesterified trisubstitute of the formula:

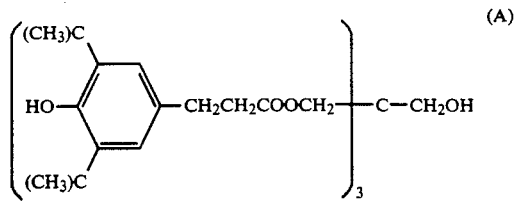

has been produced as a by-product. In order to prevent compound (A) from remaining since this is difficult to remove, Japanese Patent Publication 60-13015 (1985) provides and discloses a method for producing the tetrakisester compound wherein dipentaerithritol is added to pentaerithritol in an amount of 0.1–1.0% thereof, whereby the yield of compound (A) is reduced to less than 5%. This is also disadvantageous in that the particular substance must be added.

Hence, in order to produce sterically hindered phenol compounds useful as an antioxidant for organic materials with high quality and economically, such a catalyst is desired that fulfills the conditions: (1) the reaction solution after the termination of the reaction is not colored, (2) the removal of the catalyst is easy, and (3) no specific substance need be added to suppress the formation of byproducts.

The present inventors have investigated intensively with a view toward solving the problems noted above and accomplished this invention by finding that hindered phenol compounds can be produced by the use of monoalkyltin compounds as a catalyst without coloring, with the result that the removal of the catalyst is facilitated and the content of impurities is low.

SUMMARY OF THE INVENTION

The present invention consists in providing a novel process for the production of ester compounds represented by the formula:

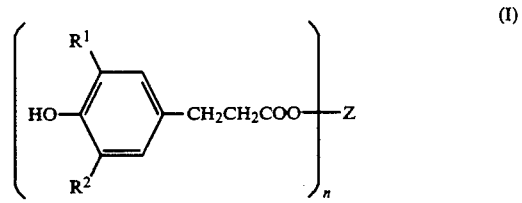

wherein $R^1$ and $R^2$ are the same or different hydrogen or straight or branched chain alkyl radicals containing 1–8 carbon atoms, Z stands for an organic radical derived from an n-hydroxy alcohol, and n denotes an integer of 1 to 4.

DETAILED DESCRIPTION OF THE INVENTION

According to this invention, the novel process for the production of ester compounds of formula (I) is characterized by subjecting a compound of the formula:

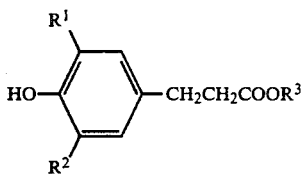 (II)

wherein $R^3$ denotes a straight or branched chain alkyl radical containing 1–8 carbon atoms and the other symbols are the same as above, and a compound of the formula:

$$Z—(—OH)_n \quad (III)$$

wherein the respective symbols are the same as above, to transesterification in the presence of a monoalkyltin compounds as a catalyst.

In the definition above, the straight or branched chain alkyl radical containing 1 to 8 carbon atoms represented by $R^1$, $R^2$, $R^3$ includes methyl, ethyl, propyl, isopropyl, butyl, sec-butyl, tert-butyl, pentyl, isopentyl, neopentyl, hexyl, octyl, 2-ethylhexyl, 1,1,3,3-tetramethylbutyl or the like. Preferred are methyl and ethyl for the alkyl radical of $R^3$.

Where n is 1, Z is a straight or branched chain alkyl radical containing 1 to 8 carbon atoms, for example, ethyl, propyl, isopropyl, butyl, isobutyl, sec-butyl, tert-butyl, pentyl, isopentyl, neopentyl, hexyl, octyl, 2-ethylhexyl, 1,1,3,3-tetramethylbutyl, decyl, dodecyl, tetradecyl, hexadecyl, octadecyl or the like.

Where n is 2, Z is an alkylene radical containing 1 to 18 carbon atoms, for example, ethylene, trimethylene, tetramethylene, hexamethylene, 2,2-dimethylmethylene, octamethylene, decamethylene, dodecamethylene, octadecamethylene and the like. As the case may be, the alkylene radical may be substituted or interposed by oxygen, sulfur, an alkyl radical or imino group. Such examples are —(CH$_2$)$_2$—S—(CH$_2$)$_2$—, —(CH$_2$)$_2$—O—(CH$_2$)$_2$—O—(CH$_2$)$_2$—.

Further example is a radical of the formula:

, wherein $R^4$, $R^5$, $R^6$, $R^7$ are the same or different and represent hydrogen or straight or branched chain alkyl radicals containing 1 to 8 carbon atoms whose examples are the same as those of $R^1$, $R^2$, $R^3$; or $R^4$ and $R^5$ or $R^6$ and $R^7$ may link to each other to form a ring of 5 to 10 carbon atoms (the ring-forming radical is an alkylene radical, for example, tetramethylene, pentamethylene, nonamethylene).

Where n is 3, Z is a radical of the formula:

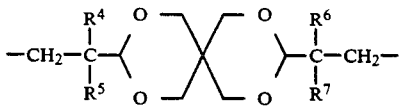

wherein p, q are the same or different integers of 1 to 4.

Where n is 4, Z is pentaerithrityl radical, i.e., C(CH$_2$)$_4$—or a radical of

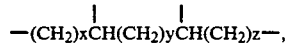

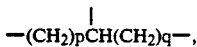

wherein x, z represent the same or different integers of 1 to 4, and y represents 0, 1, 2.

Particularly preferred compound (II) includes methyl 3-(3,5-di-tert-butyl-4-hydroxyphenyl) proprionate, methyl 3-(3-tert-butyl-4-hydroxy-5-methylphenyl)-propionate.

The compound of formula (III) includes, for example, octadecyl alcohol, triethylene glycol, pentaerithritol, 3,9-bis(2-hydroxy-1,1-dimethylethyl)-2,4,8,10-tetraoxaspiro [5-5]-undecane.

The compound of formula (I) which can be produced by the process of this invention, accordingly, includes, for example, octadecyl 3-(3,5-di-tert-butyl-4-hydroxyphenyl)propionate, triethylene glycol bis[3-(3-tert-butyl-4-hydroxy-5-methyl-phenyl)propionate], tetrakis[3-(3,5-di-tert-butyl-4-hydroxyphenyl)propionyloxymethyl]methane, 3,9-bis{2-[3-(3-tert-butyl-4-hydroxy-5-methylphenyl)priopionyloxy]-1,1-dimethylethyl}-2,4,8,10-tetraoxaspiro[5·5] undecane etc., but is not limited to them.

The monoalkyltin compounds to be used for the process of this invention include, for example, monoalkyltin oxides, monoalkyltin sulfides, monoalkyltin trihalides, monoalkyltin dihydroxyhalides, monoalkyltin tricarboxylates, monoalkyltin tris(alkylmercaptocarboxylates), etc., wherein the alkyl radical means a straight-chain or branched alkyl containing 1 to 12 carbon atoms and includes preferably, methyl, ethyl, propyl, butyl, octyl. Examples of such compounds include monobutyltin oxide, monobutyltin sulfide, monobutyltin trioctanoate, monobutyltin dilaurate, monobutyltin tris(isooctyl-mercaptoacetate), etc. Other monoalkyltin compounds can also be used, for example, monoalkyltin monocarboxylates, e.g., monoalkyltin monoacetate, monobutyltin 2-ethylhexanoate, etc. These catalysts may be used alone or in combination thereof.

The amount of the catalysts to be used is usually in the range of 0.01 to 20 mole %, preferably 0.1 to 5 mole % based on compound (II).

The monoalkyltin compounds to be used for the process of this invention, particularly, monobutyltin oxide is represented in the chemical formula of (C$_4$H$_9$SnOOH)n [it is also known to be represented by (C$_4$H$_9$SnO$_{1.5}$)n] according to Kogyo Kagaku Zasshi, (Journal of Industrial Chemistry), 73, [11], 2429–2434 (1970).

Having an acidity, a pKa value of between +4.8 and +4.0 and accordingly, a lower basicity than dibutyltin oxide which has a pKa value of more than 6.8, monobutyltin oxide is considered to be a Lewis acid. Because of this, under the same reaction conditions, the coloration degree of the reaction solution by monobutyltin oxide is much smaller than that by dibutyltin oxide. Thereby the major problem or defect with dibutyltin oxide catalyst that the reaction solution is colored can be solved. Further, the production of the by-product (the uncompleted trisubstitute of formula (A) above) in the transesterification of alkyl 3-(3,5-di-tert-butyl-4-hydroxyphenyl)propionates with pentaerithritol can be suppressed to less than 5% by weight without any additives such as dipentaerithritol.

The process of this invention usually proceeds, when heating is effected at 140°–220° C., preferably 160°–200°

C. under nitrogen stream or reflux of compound (II), at first under normal pressure and from then until the termination of the reaction under reduced pressure of 0.1-100 mmHg while distilling the resulting alkanol off. The reaction can also be conducted in an inert solvent such as toluene. Unreacted starting compound (II) is recovered, for example, by thin-film distillation under reduced pressure of 0.2 to 0.5 mmHg at 150°-185° C. The recovered compound (II) can be reused.

The new transesterification process of this invention has, owing to the use of the monoalkyltin compounds, the advantages that (1) the reaction solution is not colored, (2) no specific substance need be added, and (3) the removal of the catalyst is easy, and gives the intended products with high quality in a high yield. Thus it is of great value in terms of industriallization.

The reaction products as produced may be purified by conventional means of recrystallization, distillation, etc.

The invention is further explained by the following examples.

EXAMPLE 1

(1) Into a 500-ml four-necked flask fitted with a stirrer, a thermometer and a vacuum regulating valve are introduced 210.0 g of methyl 3-(3,5-di-tert-butyl-4-hydroxy-phenyl)propionate, 150.0 g of octadecyl alcohol, and 0.1 g of monobutyltin trilaurate, and the mixture was heated at 185°-190° C. under a diminished pressure of 20 mmHg for 1 hour and the resulting methanol was distilled off. Further heating was continued at 185°-190° C. under a reduced pressure of 3-1 mmHg for 7 hours and the methanol was further distilled off. After returning to normal pressure, the reaction was completed. A portion of the reaction product was sampled and analyzed by high speed liquid chromatography, and it was found that the product contained 289 g of octadecyl 3-(3,5-di-tert-butyl-4-hydroxyphenyl)propionate. The yield based on the added octadecyl alcohol was 98%.

(2) The procedure of Example 1(1) above was repeated except that in place of the monobutyltin trilaurate, 0.1 g of monobutyltin oxide, 0.04 g of monobutyltin trichloride, 0.03 g of monobutyltin dihydroxychloride, 0.1 g of monobutyltin tris(isooctylmercaptoacetate) or 0.03 g of monobutyltin sulfide was used, and transesterification was similarly performed. Octadecyl 3-(3,5-di-tert-butyl-4-hydroxyphenyl)-propionate was thus obtained in a yield of 97-99%.

(3) To a 300 ml toluene solution of octadecyl 3-(3,5-di-tert-butyl-4-hydroxyphenyl)propionate (tin content: 200 ppm) which was produced by the transesterification of methyl 3-(3,5-di-tert-butyl-4-hydroxyphenyl)propionate and octadecyl alcohol by use of monobutyltin oxide catalyst, was added an aqueous solution of 0.1 g of oxalic acid dihydrate in 2 g of water and the mixture was stirred for 30 minutes under reflux. Dehydration under reflux was continued for 2 hours. After cooling to about 100° C., 0.2 g of synthetic magnesium silicate (produced by Mizusawa Chemical Co.) was added and the solution was stirred at 100° C. for 30 minutes. Upon filtering at 100° C., a transparent toluene solution was obtained. The determination by atomic absorption spectrophotometry yielded the result that the residual tin content was 1 ppm (removal rate: 99.5%).

(4) Octadecyl 3-(3,5-di-tertbutyl-4-hydroxyphenyl)-propionate was prepared from 124.8 g (0.427 mole) of methyl 3-(3,5-di-tert-butyl-4-hydroxyphenyl)propionate, 88.8 g (0.328 mole) of octadecyl alcohol and 0.13 g (0.0007 mole) of monobutyltin oxide. To the solution (214 g) of it was added 35 g of synthetic magnesium silicate (manufactured by Mizusawa Chemical Co.), and the solution was stirred at 60° C. for 0.5 hour. The organic layer wa separated by filtration. The residual tin content was 3 ppm (removal rate: 99.2%).

EXAMPLE 2

(1) A 1-liter four-necked flask fitted with a stirrer, a fractionating tube with condenser, a dropping funnel and a thermometer were charged with 300 g (1.2 moles) of methyl 3-(3-tert-butyl-4-hydroxy-5-methylphenyl) propionate, 85.6 g (0.57 mole) of triethylene glycol and 0.9 g (0.00431 mole) of monobutyltin oxide, and the mixture was subjected to reaction at 170° C. for 14 hours while dropwise adding toluene. The resulting methanol was distilled off, together with the added mixture was cooled to 115° C., 260 g of toluene was added to dissolve it homogeneously. The solution was washed with 200 g (0.11 mole) of 5% oxalic acid water at 80° C. and then with 200 g of water twice to partition the solution. The toluene layer was concentrated at 120° C. under 30 mmHg to result in a pale yellow sticky substance. The pale yellow sticky substance thus obtained was recrystallized from methanol-water to afford 315 g of white crystals of triethylene glycol bis-[3-(3-tert-butyl-4-hydroxy-5-methylphenyl) propionate] as intended. Yield: 94%, residual tin content: 2 ppm, transmittance: 99% (by spectrophotometry at 425 nm).

(2) Into a 1-liter four-necked flask equipped with a stirrer, a condenser, a thermometer, and a nitrogen introducing tube were introduced 327.9 g (1.31 moles) of methyl 3-(3-tert-butyl-4-hydroxy-5-methylphenyl) propionate, 85.6 g (0.57 mole) of triethylene glycol, and 0.9 g (0.00431 mole) of monobutyltin oxide. The mixture was allowed to react at 170° C. for 1 hour, and the resulting methanol was distilled off. The reaction was continued for further 8 hours under a reduced pressure of 60-70 mmHg while bubbling nitrogen gas into the solution and thus completed. Excess methyl 3-(3-tert-butyl-4-hydroxy-5-methylphenyl) propionate was distilled off in an amount of 40.5 g at 150°-185° C. under 0.5 -0.2 mmHg by thin film distillation. This distillate can be reused, as it is, for the next reaction. Then, the reaction mixture was cooled to 115° C. and returned to atmospheric pressure by the introduction of nitrogen gas, and dissolved homogeneously by adding 260 g of toluene.

The solution was washed with 200 g (0.11 mole) of 5% oxalic acid water at 80° C. and then with 200 g of water twice for partitioning to two layers. The toluene layer was concentrated at 120° C. under 30 mmHg to give a pale yellow tacky substance. The pale yellow tacky substance so obtained was recrystallized from methanol-water to Yield 317.8 g of white crystals of triethylene glycol bis[3-(3-tert-butyl-4-hydroxy-5-methylphenyl)propionate] as intended. Yield: 95%, residual tin content: 2 ppm.

(3) The procedure of Example 2(1) above was repeated except that methyl 3-(3-tert-butyl-4-hydroxy-5-methylphenyl)-propionate was used in an amount of 470.6 g (1.88 moles) instead of 327.9 g. Yield: 95%, residual tin content: 2 ppm.

COMPARATIVE EXAMPLE 1

(1) The procedure of Example 2(1) was repeated except that the same mole of dibutyltin oxide was used instead of the monobutyltin oxide. Yield: 89%, residual tin content: 30 ppm.

(2) The procedure of Example 2(2) was repeated except that the same mole of dibutyltin oxide was used instead of monobutyltin oxide. Yield: 90%, residual tin content: 32 ppm.

EXAMPLE 3

(1) Into a 500-ml four-necked flask equipped with a stirrer, a condenser, a thermometer, and a nitrogen introducing tube were introduced 172.8 g (0.69 mole) of methyl 3-(3-tert-butyl-4-hydroxy-5-methylphenyl)propionate, 91.3 g (0.30 mole) of 3,9-bis(2-hydroxy-1,1-dimethylethyl)-2,4,8,10-tetra-oxaspiro[5.19 5] undecane and 0.79 g (0.0038 mole) of monobutyltin oxide. The mixture was allowed to react at 195° C. for 2 hours and the resulting methanol was distilled off. The reaction was continued under a reduced pressure of 5–10 mmHg for further 10 hours. A portion of the reaction product was analyzed by high speed liquid chromatography and it was found that the product contained 240 g of 3,9-bis{2-[3-tert-butyl-4-hydroxy-5-methylphenyl)propionyloxy]-1,1-dimethylethyl}-2,4,8,10-tetraoxaspiro[5·5] undecane as intended. The yield based on 3,9-bis(2-hydroxy-1,1-dimethylethyl)-2,4,8,10-tetra-oxaspiro[5·5]0 undecane added was 97%.

(2) The procedure of Example 3(1) above was repeated except that 1.0 g of monobutyltin trichloride, 0.9 g of monobutyltin dihydroxychloride or 2.0 g of monobutyltin trilaurate was used instead of the monobutyl oxide, and similar transesterification was performed. The intended product was obtained in a yield of 95–98%.

EXAMPLE 4

(1) In a 500-ml four-necked flask fitted with a stirrer, a condenser, a thermometer, and a nitrogen introducing tube, 182.7 g (0.625 mole) of methyl 3-(3,5-di-tert-butyl-4-hydroxy-phenyl)propionate, 18.9 g (0.139 mole) of pentaerithritol and 0.73 g (0.0035 mole) of monobutyltin oxide were placed and allowed to react at 185° C. for 1 hour. The resulting methanol was distilled off. The reaction was further continued for 13 hours under a reduced pressure of 60–70 mmHg by bubbling nitrogen gas into the solution (2NL/HR) and completed. Upon completion of the reaction, unesterified trisubstitute (A) in the mixture was less than 5% HPLC(s/s).

Excess methyl 3-(3,5-di-tert-butyl-4-hydroxyphenyl)-propionate was distilled off by thin-film distillation at 150°–185° C. under 0.5–0.1 mmHg for 1 hour. The distillate was 19.5 g and the rate of distillation was 97%. This can be reused, as it is, for the next reaction.

After the reaction mixture was cooled to 115° C., nitrogen gas was admitted to it to return its pressure to atmospheric pressure, and the reaction mixture was dissolved homogeneously by toluene.

The toluene solution above (tin content: 700 ppm) was washed with 400 g (0.16 mole) of 5% oxalic acid water and then with 40 g of water twice at 60° C. to partition the solution to two layers. The toluene layer was concentrated at 125° C. under 30 mmHg for 1 hour to give a pale yellow tacky substance. When recrystallized from methanol, the pale yellow tacky substance so obtained afforded 147.8 g of tetra-kis [3-(3,5-di-tert-butyl-4-hydroxyphenyl)propionyloxymethyl]-methane in white crystals as intended. yield: 87%, residual tin content: 1 ppm, (removal rate: more than 99.9% by atomic absorption spectrophotometry), transmittance: 98% (spectrophotometry at 425 nm).

(2) The procedure of Example 4(1) above was repeated except that methyl 3-(3,5-di-tert-butyl-4-hydroxyphenyl)-propionate was used in an amount of 268.2 g (0.917 mole) in place of 182.7 g. Yield: 85%, residual tin content: 1 ppm (removal rate: more than 99.9%), transmittance: 95%.

EXAMPLE 5

(1) In a 500-ml four-necked flask fitted with a stirrer, a thermometer, and a vacuum regulating valve, 292.4 g of methyl 3-(3,5-di-tert-butyl-4-hydroxyphenyl)propionate, 22.7 g of pentaerithritol and 3.2 g of monobutyltin trilaurate were placed and heated at 185°–190° C. for 1 hour, and the resulting methanol was distilled off. Heating was further continued at 185°–190° C. under 70 mmHg for 5 hours and the resulting methanol was distilled off. After returning to atmospheric pressure, the reaction was completed. A portion of the reaction product was taken and analyzed by high speed liquid chromatography and it was found that the product contained 190 g of tetrakis[3-(3,5-di-tert-butyl-4-hydroxyphenyl) propionyloxymethyl] methane as intended. The yield based on the added pentaerithritol was 97%.

(2) The procedure of Example 5(1) above was repeated except that the catalyst was replaced by 1.2 g of monobutyltin trichloride, and the intended product was obtained in a yield of 96%.

Again, the transesterification was similarly performed each by use of monobutyltin dihydroxychloride, monobutyltin tris(isooctylmercaptoacetate), monobutyltin sulfide or monobutyltin trioctanoate, and in all the cases, the intended products were obtained in good yields.

EXAMPLE 6

Into a 1-liter four-necked flask equipped with a stirrer, a condenser, a thermometer and a nitrogen-introducing tube, 671.6 g (2.3 mole) of methyl 3-(3,5-di-tert-butyl-4-hydroxy-phenyl)propionate, 68.0 g (0.50 mole) of pentaerithritol, 2.25 g (10.9 mmol) of monobutyltin oxide, 0.16 g (0.57 mmol) of monobutyltin trichloride (the total amount of the catalysts corresponds to 0.5 mole % based on the propionate compound) and 100 g of toluene were charged and allowed to react with stirring at 170°–175° C. for 12 hours. During the reaction, 500 g of toluene was added dropwise and distilled off together with the resulting methanol. After the termination of the reaction, 200 g of toluene was added to dissolve the reaction product, and 200 g of 5 wt. % oxalic acid water was added and stirred for 1 hour. The solution was allowed to stand still and the water layer so separated was removed. The organic layer was washed with 200 g of water twice and then, toluene was distilled off under diminished pressure. Excess ester compound as a starting material was recovered by vacuum distillation. The recovered ester was 85.8 g (recovery: 98%). Thus, a syrupy substance, 590 g, was obtained, and when recrystallized from 148 g of 95 wt. % methanol-water, afforded 577.1 g (yield: 98.0%) of tetrakis[3-(3,5-di-tert-butyl-4-hydroxyphenyl)propionyloxymethyl]methane in white crystals.

COMPARATIVE EXAMPLE 2

The procedure of Example 4 was repeated except that the same mole proportion of dibutyltin oxide was used in place of the monobutyltin oxide.

The treatment of the monoalkyltin compound was carried out in the procedure of Example 4, and the resulting filtrate solution was concentrated to obtain an yellowish brown sticky substance. The crystallization of this substance from methanol afforded the intended product. Yield: 80%, residual tin content: 30 ppm (removal rate: 98%), transmittance: 95%.

We claim:

1. A process for producing an ester compound of the formula:

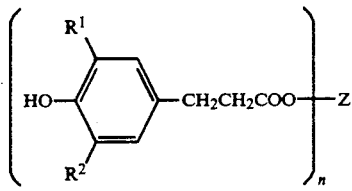

wherein $R^1$ and $R^2$ are the same or different and represent hydrogen or straight or branched chain alkyl radicals containing 1-8 carbon atoms, Z is an organic radical derived from an n-hydroxy alcohol, and n denotes an integer of 1 to 4, which comprises subjecting a compound of the formula:

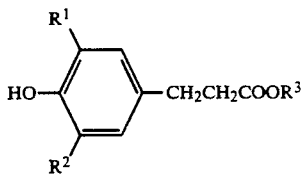

wherein $R^1$ and $R^2$ have the same definition as above, and $R^3$ is a straight or branched chain alkyl radical containing 1-8 carbon atoms, and a compound of the formula:

$$Z-OH)_n$$

wherein the respective symbols are the same as above, to transesterification in the presence of a monoalkyltin compound as a catalyst.

2. The process as set forth in claim 1, wherein said monoalkyltin compound is selected from the group consisting of monoalkyltin oxides, monoalkyltin sulfides, monoalkyltin trihalides, monoalkyltin dihydroxyhalides, monoalkyltin tri-carboxylates, and monoalkyltin tris(alkylmercaptocarboxylates).

3. The process as set forth in claim 1, wherein said monoalkyltin compound is monobutyltin oxide.

* * * * *